United States Patent
Tverskoy et al.

(10) Patent No.: US 8,522,338 B2
(45) Date of Patent: Aug. 27, 2013

(54) TWO-WAY AUTHENTICATION

(75) Inventors: Mark Tverskoy, Andover, MA (US); Anthony Ralph Diciaccio, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 13/379,500

(22) PCT Filed: Jun. 22, 2009

(86) PCT No.: PCT/US2009/048166
§ 371 (c)(1),
(2), (4) Date: Dec. 20, 2011

(87) PCT Pub. No.: WO2010/151246
PCT Pub. Date: Dec. 29, 2010

(65) Prior Publication Data
US 2012/0110661 A1   May 3, 2012

(51) Int. Cl.
*G06F 7/04*   (2006.01)

(52) U.S. Cl.
USPC .......................................................... 726/16

(58) Field of Classification Search
USPC .......................................................... 726/16
See application file for complete search history.

(56) References Cited

U.S. PATENT DOCUMENTS

| | | | |
|---|---|---|---|
| 5,960,085 | A | 9/1999 | de la Huerga |
| 6,789,191 | B1* | 9/2004 | Lapstun et al. ............... 713/168 |
| 7,060,031 | B2 | 6/2006 | Webb et al. |
| 7,127,300 | B2 | 10/2006 | Mazar et al. |
| 2007/0204342 | A1* | 8/2007 | Markovich et al. ............. 726/23 |
| 2008/0209545 | A1 | 8/2008 | Asano |

OTHER PUBLICATIONS

International search report for PCT/IS2009/048166, published as WO 2010/151246.

* cited by examiner

*Primary Examiner* — Jacob Lipman
(74) *Attorney, Agent, or Firm* — Driggs, Hogg, Daugherty & Del Zoppo, Co. LPA

(57) ABSTRACT

A method for activating a physiologic sensor (124) of a peripheral device (104) of a monitoring apparatus (100) includes receiving, at the peripheral device (104), a signal indicating a host device (102) authenticated the peripheral device (104), receiving, at the peripheral device (104), a host device authentication response signal, authenticating, at the peripheral device (104), the host device (102) based on the host device authentication response signal, and activating the physiologic sensor (124) of the peripheral device (104) in response to authentication of both the host and peripheral devices (102, 104).

28 Claims, 3 Drawing Sheets

TWO-WAY AUTHENTICATION

RELATED APPLICATION

This application is a national filing of PCT application Serial No. PCT/US2009/048166, filed Jun. 22, 2009, published as WO2010/151246 on Dec. 29, 2010.

TECHNICAL FIELD

The following generally relates to two-way authentication and is described with particular application to physiologic parameter monitoring. However, it is also amenable to other medical and non-medical applications.

BACKGROUND

Physiological parameter monitors have included a combination of a host monitoring device (host device) and a single or multiple peripheral sensing devices (peripheral device) which are connected to the host device. The peripheral device(s) usually includes a connector that attaches to the complimentary connector on the host device side. Once the peripheral device connector is coupled to the host device, the peripheral device function is activated by the host monitoring device. Unfortunately, with such a connection configuration, the host monitor may not be able to tell whether a proper peripheral device is attached. As a consequence, an improper peripheral device can be plugged into the host monitoring device (assuming the physical shapes of the respective connectors allow for such mating) and the host monitor may be programmed by the user as if the intended peripheral device was connected. Likewise, the peripheral device may not be able to distinguish whether the host monitor attached to it is intended for proper coupling. As a consequence, the peripheral sensing device can be connected with the incorrect host monitoring device and the incorrect host device may be programmed by the user as if the proper peripheral device was connected thereto.

SUMMARY

Aspects of the application address the above matters, and others.

In one aspect, a method for activating a physiologic sensor of a peripheral device of a monitoring apparatus is discussed. The method includes receiving, at the peripheral device, a signal indicating a host device authenticated the peripheral device. The method further includes receiving, at the peripheral device, a host device authentication response signal. The method further includes authenticating, at the peripheral device, the host device based on the host device authentication response signal. The method further includes activating the physiologic sensor of the peripheral device in response to authentication of both the host and peripheral devices.

In another aspect, a physiologic parameter monitoring apparatus includes a host device with a peripheral device authenticator and a peripheral device with a host device authenticator and a sensor that senses a physiologic state of a patient. The peripheral device authenticator authenticates the peripheral device and the host device authenticator authenticates the host device, and the sensor is activated in response to two-way authentication of the host and peripheral devices.

In another aspect, a method includes activating a physiologic sensor of a peripheral device based on two-way authentication between the peripheral device and the host device.

In another aspect, a method for activating a physiologic sensor of a peripheral device of a monitoring apparatus is discussed. The method includes receiving, at a host device, a signal indicating the peripheral device authenticated the host device. The method further includes receiving, at the host device, a peripheral device authentication response signal. The method further includes authenticating, at the host device, the peripheral device based on the peripheral device authentication response signal. The method further includes activating the physiologic sensor of the peripheral device in response to authentication of both the host and peripheral devices.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
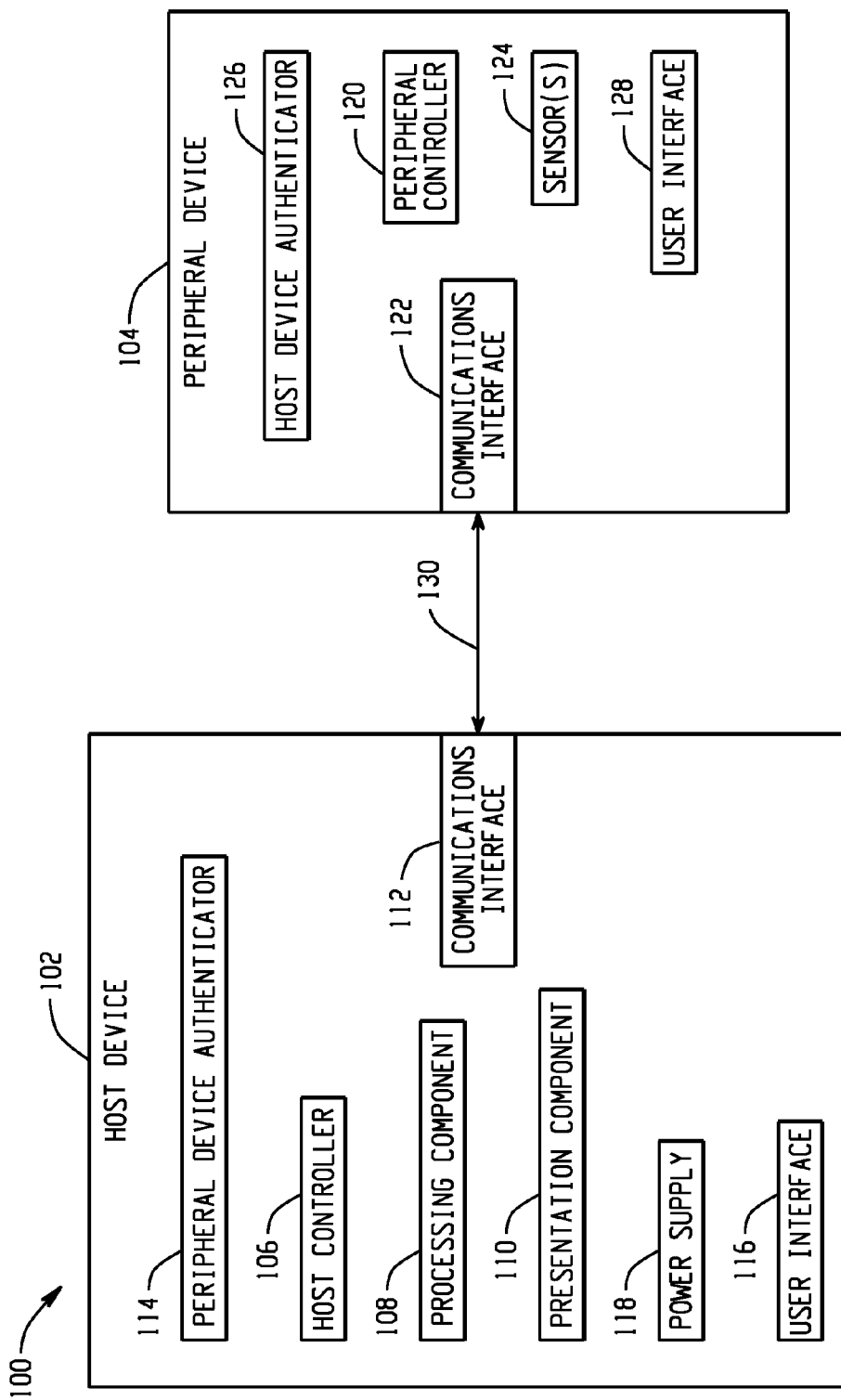
FIG. 1 illustrates an example physiologic parameter monitoring system.

FIG. 1 illustrates an apparatus 100 that includes a host device 102 and at least one peripheral device 104. An example of such an apparatus includes a patient temperature monitoring apparatus with a temperature-sensing probe (peripheral device) that removably attaches via a cable or the like to a monitor unit (host device) that displays the sensed temperature. Other suitable apparatuses include, but are not limited to, blood pressure, heart rate and/or other physiologic parameter monitors, and/or non-physiologic parameter monitors.

The host device 102 includes a microprocessor or host controller 106 that controls overall operation of the host device 102. The host controller 106 also transmits and/or receives signals to and from the peripheral device 104. A processing component 108 processes data such as sensed data obtained from the peripheral device 104 and/or input by a user. A presentation component 110 presents processed data, messages, warning, alarms, and/or other information in a human readable format.

A communications interface 112, with input and output ports, is configured for communicating signals with the peripheral device 104. A user interface 116 accepts input provided by a user to the host device 102. A power supply 118 provides power for powering the host and/or peripheral devices 102 and 104. The power supply 118 provides power from a power source such as a battery, wall outlet alternating current, and/or other power source. The host device 102 also includes a peripheral device authenticator 114. As described in greater detail below, the peripheral device authenticator 114 facilitates host device authentication of the peripheral device 104.

The peripheral device 104 includes a microprocessor or peripheral controller 120 that controls overall operation of the peripheral device 104. The peripheral controller 120 transmits and/or receives signals to and from the host device 102. At least one physiologic sensor 124 senses a signal indicative of a physiologic state (e.g., temperature, blood pressure, heart rate, etc.) of a patient. The illustrated physiologic sensor 124 is configured to be in an inactive initial state when the peripheral device 104 is powered up. As described in greater detail below, the illustrated sensor 124 transitions to an active state based on two-way authentication between the host and peripheral devices 102 and 104.

A communications interface 122, with input and output ports, is configured for communicating signals. A user interface 128 accepts input provided by a host device to the peripheral device 104. The illustrated peripheral device 104 is powered with power supplied by the host device 102 through the communications interface 122. The peripheral device 104 further includes a host device authenticator 126. As described in greater detail below, the host device authenticator 126 facilitates peripheral device authentication of the host device 102.

The host and peripheral devices 102 and 104 communicate with each other through their respective communications interfaces 112 and 122 over a suitable communications link 130, which may be a cable or the like, or a wireless communications medium. In the illustrated embodiment, the host and peripheral devices 102 and 104 are configured to authenticate each other (two-way authentication), and at least one sensor 124 is selectively activated based on two-way authentication. In one instance, this allows for determining whether the host and peripheral devices 102 and 104 are permitted to operate with each other before allowing the sensor 124 to be activated.

Figure 2:
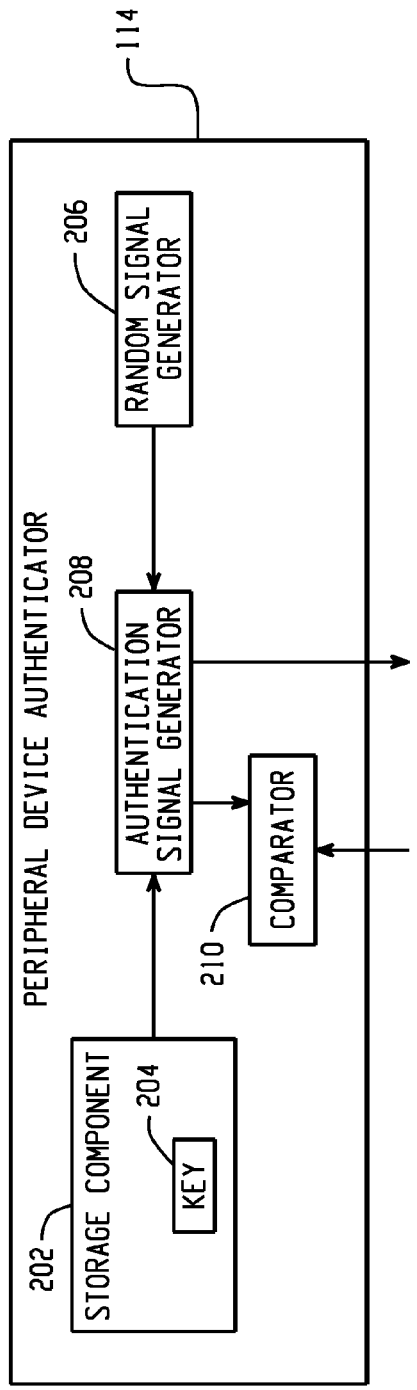
FIG. 2 illustrates an example host authenticator.
Figure 3:
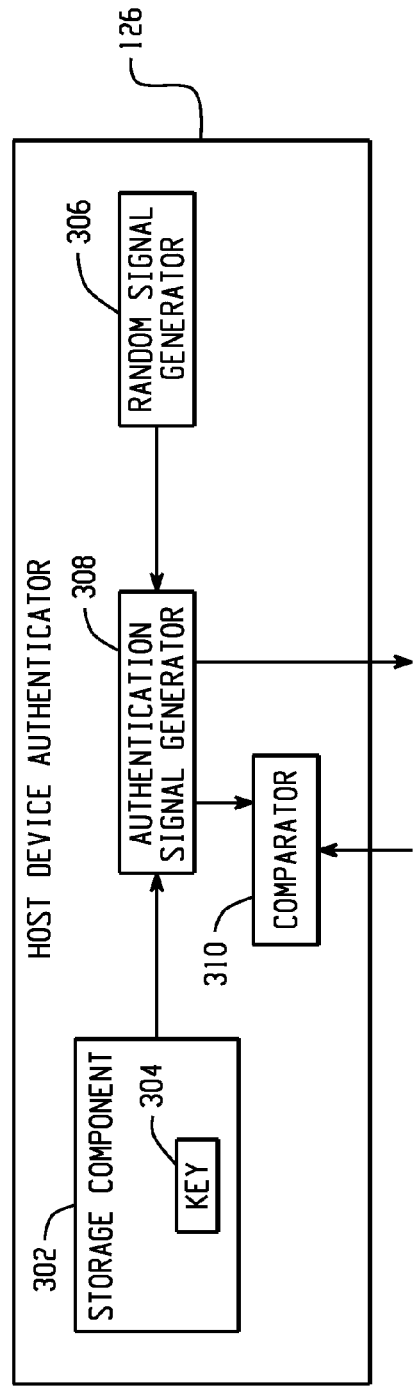
FIG. 3 illustrates an example peripheral authenticator.

FIGS. 2 and 3 respectively illustrate examples of the authenticators 114 and 126.

Initially referring to FIGS. 1 and 2, the peripheral device authenticator 114 of the host device 102 includes a storage component 202 with at least one key 204 and a random signal generator 206 that generates random signals. The key(s) stored in the storage component 202 correspond to one or more peripheral devices 104 pre-validated for use with the host device 102.

An authentication signal generator 208 generates authentication signals, including an authentication request signal based on a random signal from the random signal generator 206, an authentication compare signal based on the random signal and the key 204, and an authentication response signal based on a random signal from the peripheral device 104.

The peripheral device authenticator 114 also includes a comparator 210 that compares the authentication compare signal with an authentication response signal generated by the peripheral device 104, and generates a signal indicative of the comparison.

Turning to FIGS. 1 and 3, the host device authenticator 126 of the peripheral device 104 includes a storage component 302 with at least one key 304 (which, in the illustrated embodiment, is indicative of a same value as the key 204) and a random signal generator 306. The key(s) stored in the storage component 302 correspond to one or more host devices 102 pre-validated for use with the peripheral device 104.

An authentication signal generator 308 generates authentication signals, including an authentication request signal based on a random signal from the random signal generator 306, an authentication compare signal based on the random signal and the key 304, and an authentication response signal based on a random signal from the host device 102.

The host device authenticator 126 also includes a comparator 310 that compares the authentication compare signal with an authentication response signal generated by the host device 102, and generates a signal indicative of the comparison.

With respect to FIGS. 1, 2 and 3, the host device 102 authenticates the peripheral device 104, and vice versa. For host device authentication of the peripheral device 104, the authentication signal generator 208 of the host device 102 generates an authentication request signal and an authentication compare signal. The authentication request signal is transmitted to the peripheral device 104. The peripheral device 104, in response to receiving the authentication request signal, generates an authentication response signal. In the illustrated embodiment, the peripheral device 104 generates the authentication response signal based on a secure algorithm such as a secure cryptographic, hash or other secure algorithm. The authentication response signal is transmitted to the host device 102.

The comparator 210 of the host device 102 compares the received authentication response signal and the generated authentication compare signal. The output of the comparator 210 is indicative of whether the signals match. If the signals match, the host device 102 authenticates the peripheral device 104, and the host controller 106 may send a signal to the peripheral device 104, notifying the peripheral device 104 that the peripheral device 104 is authenticated by the host device 102. If the two signals do not match, the host device 102 does not authenticate the peripheral device 104. In this case, a message indicating unsuccessful authentication may be displayed via the presentation component 110.

Still referring to FIGS. 1, 2 and 3, for peripheral device authentication of the host device 102, the authentication signal generator 308 of the peripheral device 104 generates an authentication request signal and an authentication compare signal. The authentication request signal is transmitted to the host device 102. The host device 102, in response to receiving the authentication request signal, generates an authentication response signal. In the illustrated embodiment, the host device 102 also generates the authentication response signal based on a secure algorithm such as a secure cryptographic, hash or other secure algorithm. The authentication response signal is transmitted to the peripheral device 104.

The comparator 310 of the peripheral device 104 compares the received authentication response signal and the generated authentication compare signal. The output of the comparator 310 is indicative of whether the signals match. If the signals match, the peripheral device 104 authenticates the host device 102, and the peripheral device controller 120 may send a signal to the host device 102, notifying the host device 102 that the host device 102 is authenticated by the peripheral device 104. If the two signals do not match, the peripheral device 104 likewise does not authenticate the host device 102. Again, message or other indicia indicating unsuccessful authentication may be displayed via the presentation component 110.

When both the host and the peripheral devices 102 and 104 have authenticate each other (2-way authentication), the sensor 124 is activated by the peripheral device 104. If the authentication signals do not match, the peripheral device 104 does not activate the sensor 124.

Various embodiments are discussed.

In another embodiment, an unsecure authentication approach is employed. In such an embodiment, the authentication signals are not generated based on random signals and/or secure authentication algorithms.

In another embodiment, the order of authentication is reversed. That is, the host device 102 is first authenticated and then the peripheral device 104 is authenticated.

In yet another embodiment, the host and peripheral devices 102 and 104 concurrently authenticate each other.

In another embodiment, a user of the apparatus 100 can override successful and/or unsuccessful authentication.

In another embodiment, the peripheral device 104 includes its own power supply.

In another embodiment, the host device 102 activates the sensor 124.

In another embodiment, a one-way authentication approach, either authentication of the peripheral device 104 or the host device 102, is utilized.

In another embodiment, matching authentication signals may results in actively preventing activation of the sensor 124.

Figure 4:
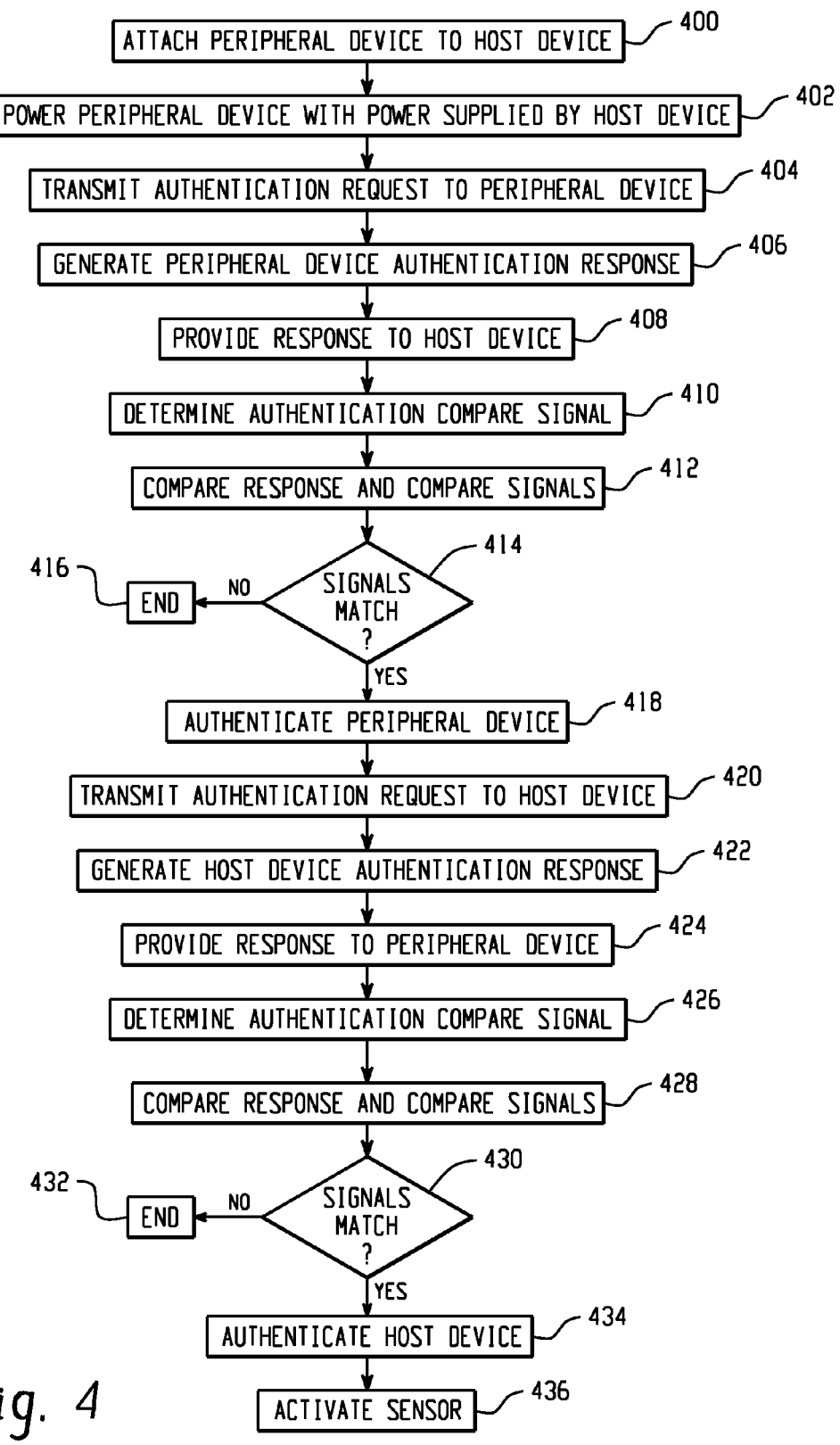
FIG. 4 illustrates an example method.

FIG. 4 illustrates a non-limiting example method of suitable two-way secure authentication using a secure hashing algorithm. It is to be appreciated that the ordering of the acts is for explanatory purposes and not limiting. In addition, other embodiments may include more or less, including different, acts.

At 400, the host and peripheral devices 102 and 104 are coupled via respective communication interfaces 112 and 122.

At 402, the host device 102 supplies power for the peripheral device 104.

At 404, the host device 102 transmits an authentication request to the peripheral device 104. As noted herein, in one embodiment the authentication request includes a random signal generated by the host device 102.

At 406, the peripheral device 104 generates a peripheral device authentication response signal in response to the received authentication request. In the illustrated embodiment, the peripheral device authentication response signal is based on the received authentication request and a key 304.

At 408, the peripheral device 104 transmits the peripheral device authentication response signal to the host device 102.

At 410, the host device 102 determines an authentication compare signal based on the random signal and a key 204 of the host device 102. The keys 204 and 304 may represent the same known value common to both the host and peripheral devices 102 and 104.

At 412, the host device 102 compares the response and compare signals.

At 414, if the response and compare signals do not match, then at 416 the host device 102 does not authenticate the peripheral device 104.

If at 414 the response and compare signals match, then at 418 the host device 102 authenticates the peripheral device 104. Authentication may include transmitting an authentication confirmation signal to the peripheral device 104.

At 420, in response to authenticating the peripheral device, the peripheral device 104 transmits an authentication request signal to the to the host device 102. In one embodiment, the authentication request includes a random signal generated by the peripheral device 104.

At 422, the host device 102 generates a host device authentication response signal in response to the received authentication request. In the illustrated embodiment, the host device authentication signal is based on the request and the key 204.

At 424, the host device 102 transmits the host device authentication response signal to the peripheral device 104.

At 426, the peripheral device 104 determines an authentication compare signal based on the random signal and the key 304.

At 428, the peripheral device 104 compares the response and compare signals.

At 430, if the response and compare signals do not match, then at 432 the peripheral device 104 does not authenticate the host device 102.

If at 430 the response and compare signals match, then at 434 the peripheral device 104 authenticates the host device 102.

At 436, the sensor 124 is activated based on the two-way authentication. As described herein, the sensor 124 may be activated by the host device 102 in one embodiment and by the peripheral device 104 in another embodiment.

As described herein, in another embodiment the peripheral device 104 authenticates the host device 102 and then the host device 102 authenticates the peripheral device 104, and in another embodiment, the host and peripheral devices 102 and 104 concurrently authenticate each other.

Another method includes authenticating the peripheral device 104 by the host device 102, authenticating the host device 102 by the peripheral device 104, and activating the physiologic sensor 124 of the peripheral device 104 in response to authentication of the host and peripheral devices 102, 104.

The above may be implemented by way of computer readable instructions, which when executed by a computer processor(s), cause the processor(s) to carry out the acts. The instructions can be stored in a computer readable storage medium associated with or otherwise accessible to the relevant computer.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method for activating a physiologic sensor of a peripheral device of a monitoring apparatus, comprising:
   receiving, at the peripheral device, a signal indicating a host device authenticated the peripheral device;
   receiving, at the peripheral device, a host device authentication response signal;
   authenticating, at the peripheral device, the host device based on the host device authentication response signal; and
   activating the physiologic sensor of the peripheral device in response to authentication of both the host and peripheral devices.

2. The method of claim 1, further comprising: authenticating at least one of the host or peripheral devices using a secure authentication algorithm.

3. The method of claim 1, wherein the physiologic sensor is activated only in response to authentication of both the host and peripheral devices.

4. The method of claim 1, further comprising: authenticating the host and peripheral devices using an unsecure authentication algorithm.

5. The method of claim 1, wherein the peripheral device activates the physiologic sensor.

6. The method of claim 1, wherein the host device activates the physiologic sensor.

7. The method of claim 1, further comprising: activating the sensor in response to two-way authentication of both the host and peripheral devices.

8. The method of claim 7, wherein the sensor remains in an inactive state in response to unsuccessful authentication of at least one of the host and peripheral devices.

9. The method of claim 1, further comprising:
   generating, at the peripheral device, an authentication compare signal; and
   authenticating the host device in response to successfully matching the received host device authentication response signal and the authentication compare signal.

10. The method of claim 9, further comprising:
    generating, at the peripheral device, a random number, wherein the authentication compare signal is based on the random number and a key of the peripheral device.

11. The method of claim 10, wherein the host device authentication response signal is based on the random number and a key of the host device.

12. The method of claim 11, further comprising:
generating, at the peripheral device, a host device authentication request signal based on the random number, wherein the host device generates and transmits the host device authentication response signal in response to receiving the host device authentication request signal.

13. A physiologic parameter monitoring apparatus, comprising:
a host device with a peripheral device authenticator; and
a peripheral device with a host device authenticator and a sensor that senses a physiologic state of a patient,
wherein the peripheral device authenticator authenticates the peripheral device and the host device authenticator authenticates the host device, and the sensor is activated in response to two-way authentication of the host and peripheral devices.

14. The apparatus of claim 13, wherein at least one of the peripheral or host device authenticators respectively authenticates the peripheral or host devices based on an unsecure authentication algorithm.

15. The apparatus of claim 13, wherein activating the sensor includes transitioning the sensor from an inactive state to an active state.

16. The apparatus of claim 13, the host device, further comprising: a power supply that supplies power to the host device and the peripheral device.

17. The apparatus of claim 13, the host device, further comprising: a presentation component that presents information indicative of a state of the two-way authentication.

18. The apparatus of claim 13, wherein the sensor senses at least one of a body temperature, a heart rate and a blood pressure of a patient.

19. The apparatus of claim 13, wherein the peripheral device activates the physiologic sensor.

20. The apparatus of claim 13, wherein the host device activates the physiologic sensor.

21. The apparatus of claim 13, wherein at least one of the peripheral or host device authenticators respectively authenticates the peripheral or host devices based on a secure authentication algorithm.

22. The apparatus of claim 21, wherein the secure authentication algorithm is a secure hashing algorithm.

23. The apparatus of claim 13, the peripheral device authenticator, including:
a first random signal generator that generates a first random signal;
first storage including a first key;
a first authentication signal generator that generates an authentication compare signal based on the first random signal and the first key; and
a comparator that compares the generated authentication compare signal with an authentication response signal provided by the host device authenticator, wherein the peripheral device authenticates the host device in response to the compare and response signals matching.

24. The apparatus of claim 23, the host device authenticator, including:
second storage including a second key; and
a second authentication signal generator that generates the authentication response signal based on the first random signal and the second key.

25. The apparatus of claim 13, the host device authenticator, including:
a first random signal generator that generates a first random signal;
first storage including a first key;
a first authentication signal generator that generates an authentication compare based on the random signal and the first key; and
a comparator that compares the generated authentication signal with an authentication response signal generated by the peripheral device authenticator, wherein the host device authenticates the peripheral device in response to the first and second authentication signals matching.

26. The apparatus of claim 25, the peripheral device authenticator, including:
second storage including a second key;
a second authentication signal generator that generates the authentication response signal based on the first random signal and the second key.

27. A method, comprising:
activating a physiologic sensor of a peripheral device based on two-way authentication between the peripheral device and the host device.

28. A method for activating a physiologic sensor of a peripheral device of a monitoring apparatus, comprising:
receiving, at the host device, a signal indicating a peripheral device authenticated the host device;
receiving, at the host device, a peripheral device authentication response signal;
authenticating, at the host device, the peripheral device based on the peripheral device authentication response signal; and
activating the physiologic sensor of the peripheral device in response to authentication of both the host and peripheral devices.

* * * * *